(12) United States Patent
Tsuchida et al.

(10) Patent No.: US 7,285,379 B2
(45) Date of Patent: Oct. 23, 2007

(54) ARTIFICIAL OXYGEN CARRIER AND PRODUCTION METHOD THEREOF

(75) Inventors: Eishun Tsuchida, Tokyo (JP); Shinji Takeoka, Tokyo (JP); Teruyuki Komatsu, Tachikawa (JP); Toshiya Kai, Osaka (JP); Naohisa Katayama, Osaka (JP); Ippei Fukutomi, Osaka (JP); Makoto Sato, Osaka (JP)

(73) Assignee: Nipro Corporation, Osaka (JP)

( * ) Notice: Subject to any disclaimer, the term of this patent is extended or adjusted under 35 U.S.C. 154(b) by 161 days.

(21) Appl. No.: 10/927,675

(22) Filed: Aug. 27, 2004

(65) Prior Publication Data

US 2005/0085410 A1 Apr. 21, 2005

(30) Foreign Application Priority Data

Aug. 28, 2003 (JP) ............................. 2003/305036

(51) Int. Cl.
- *A01N 1/02* (2006.01)
- *C12P 21/04* (2006.01)
- *C07K 14/00* (2006.01)

(52) U.S. Cl. .......................... 435/2; 435/69.6; 530/350
(58) Field of Classification Search ................ 530/350; 435/69.1; 514/12
See application file for complete search history.

(56) References Cited

U.S. PATENT DOCUMENTS 5,773,417 A * 6/1998 Bonaventura ................ 514/21
6,008,198 A * 12/1999 Tsuchida et al. ............. 514/21

FOREIGN PATENT DOCUMENTS

| JP | 08-301873 A | 11/1996 |
| JP | 10-503489 A | 3/1998 |
| JP | 2001-072595 A | 3/2001 |

OTHER PUBLICATIONS

Sue Parham, published on the web at www.aabb.org/Content/Meetings_and_Events/Annual_Meeting_and_TXPO/58amtueoxy.htm, Jan. 2006, pp. 1-2.*
Komatsu et al., *Artificial Blood*, 6(4): 110-114 (1998).
Tsuchida et al., *Bioconjugate Chem.*, 8(4): 534-538 (1997).
Tsuchida et al., *Bioconjugate Chem.*, 10(5): 797-802 (1999).

* cited by examiner

*Primary Examiner*—Robert B. Mondesi
(74) *Attorney, Agent, or Firm*—Leydig, Voit & Mayer, Ltd.

(57) ABSTRACT

The present invention provides a method of producing a complex of albumin and a deoxy form metal complex having a porphyrin structure, which includes mixing albumin and a metal complex having a porphyrin structure under a gas atmosphere substantially free of carbon monoxide and oxygen, as a method of producing an artificial oxygen carrier containing a complex of albumin and a metal complex having a porphyrin structure, under a deoxidation (nitrogen, other inert gases) atmosphere without using carbon monoxide.

11 Claims, 1 Drawing Sheet

ARTIFICIAL OXYGEN CARRIER AND PRODUCTION METHOD THEREOF

FIELD OF THE INVENTION

The present invention relates to an artificial oxygen carrier capable of reversibly adsorbing and desorbing oxygen in living organisms, and an artificial oxygen infusion preparation comprising an artificial oxygen carrier. More particularly, the present invention relates to a complex of albumin and a deoxy form metal complex having a porphyrin structure, which is highly safe and of high quality and which is used in the medical field for supply of oxygen to ischemic penumbra or tumor tissue, for blood infusion of patients with massive hemorrhage, and as an organ preservation perfusate, a solution for extracorporeal circulation or a cell culture fluid, and a production method thereof.

BACKGROUND OF THE INVENTION

It has been known that plasma protein, or plasma colloid, plays a key role in maintaining the blood flow in blood vessels of living organisms. In view of this, to make patients recover from hemorrhagic shock, a plasma expander having almost the same colloid osmotic pressure as the blood of living organisms has been conventional used as a fluid replacement. In the case of massive loss of 30% or more of the circulating blood volume, however, oxygen supply to the peripheral tissues becomes insufficient, and administration of an oxygen carrier becomes necessary in addition to the administration of a plasma expander.

As such oxygen carrier, natural blood containing natural red blood cell and a red blood cell heavy-solution have been conventionally used. To avoid blood clotting due to antigen antibody reactions, the blood types of the donor and recipient need to be matched and cross matching needs to be performed when in use. The natural blood and red blood cell heavy solution can stay effective by preservation only for a short period of 3 weeks (4° C.). On the other hand, frozen blood permitting long-term preservation by cryopreservation is problematically susceptible to high cost and hemolysis due to osmotic shock during use. In addition, occurrence of infectious diseases, such as hepatitis, AIDS and the like, has been worried.

As an oxygen carrier to solve such problems, various artificial oxygen carriers have been studied. An oxygen infusion preparation (hereinafter albumin-heme), wherein a heme derivative, 2-[8-[N-(2-methylimidazolyl)]octanoyloxymethyl]-5,10,15,20-tetrakis ($\alpha,\alpha,\alpha,\alpha$-o-pivalamido) phenylporphynatoiron complex etc., is adsorbed onto a hydrophobic pocket of human albumin or recombinant albumin, has been synthesized and its oxygen transport capability has been confirmed (E. Tsuchida, et al., Bioconjugate Chemistry, vol. 8, 534-538, 1997).

For production of these artificial oxygen carriers, toxic carbon monoxide (hereinafter CO) has been conventionally used.

Komatsu et al., Bioconjugate Chemistry, vol. 10, 797-802, 1999 (page 800, left column, line 2 from the bottom—right column line 1) describe that albumin-heme is degraded by 50% in the presence of oxygen at 25° C.: 8 hr, or at 37° C.: 2 hr. In this way, when oxygen is present in a production step, a divalent iron complex becomes trivalent and the function of oxygen carrier is not fulfilled, thereby failing to provide an albumin-heme having sufficient oxygen transport capability.

To completely block mixing of oxygen during a production step, however, an extremely highly advanced facility is required. Since general facility cannot prevent mixing of oxygen, it has been a conventional practice to use CO to produce an oxygen carrier so that the oxygen carrier will not be degraded even when oxygen is mixed in a production step. Binding of CO to a porphyrin iron complex (hereinafter abbreviated as heme) maintains divalent iron of heme at a stable level, and an oxidation reaction into a trivalent iron can be suppressed.

One example of the production method of artificial oxygen carrier using CO comprises first forming a CO-PFP by reacting picket-fence porphyrin (hereinafter PFP) with CO. This CO-PFP is further reduced with dithionite. Then, CO-PFP is mixed with human serum albumin (hereinafter HSA) to give a complex with HSA (hereinafter CO-PFP-HSA). Formation of CO-PFP-HSA can be confirmed by chromatography and ultrafiltration. CO can be removed by exposing a sample to light in a tonometer containing oxygen. By removing oxygen from the resulting $O_2$-HSA-PFP by nitrogen replacement, HSA-PFP can be obtained (JP-T-10-503489, page 14, lines 5-11).

However, to perform such a production step in a CO atmosphere, a large amount of CO is necessary, which may cause fatal damage to the human body.

In view of the foregoing, a production method free of CO in a production step and degradation of an artificial oxygen carrier has been desired.

When an artificial oxygen carrier produced in this manner is placed under chilled preservation under a CO atmosphere, degradation by oxidation reaction is similarly suppressed as described above. However, when CO is bound, due to the absence of oxygen binding capability, a step to remove CO before administration becomes necessary. CO is also generated at this stage and poses problems such as a fear of affecting human body and incapability of dealing with administration in emergency situations.

As a method to solve such problems, JP-A-2001-72595 describes (paragraph 0028) a method for preserving albumin-heme by converting the same to deoxy-heme. To be specific, after confirmation with respect of a physiological saline solution of albumin-heme prepared according to Komatsu et al., Bioconjugate Chemistry vol. 10, 797-802, 1999 (page 800, left column, line 2 from the bottom—right column, line 1) that heme is in a divalent state of iron, the dispersion is exposed to nitrogen or other inert gases (argon, helium and the like) free of oxygen to remove oxygen from this dispersion, whereby the dissolved oxygen is exhausted and oxy-heme is converted to deoxy-heme free of oxygen bond for preservation.

In this method described in JP-A-2001-72595, however, CO is not used for deoxidization in a preservation form but CO is still used in the production steps (e.g., Example 1, Example 7 of JP-A-2001-72595 and Komatsu et al., Artificial Blood, vol. 6, 110-114, 1998 (page 111, left column, lines 16-19)).

Conventional production methods of artificial oxygen carrier (e.g., hemoglobin vesicle, lipid heme vesicle, lipid heme-triglyceride microsphere, albumin-heme and the like) using CO are associated with the above-mentioned problems and a production method of a safer artificial oxygen carrier easy to handle has been desired. However, a production method of an artificial oxygen carrier free of use of CO in a production step has not been reported heretofore.

SUMMARY OF THE INVENTION

The present invention provides a method of producing a complex of albumin and a metal complex having a porphyrin structure, which is an artificial oxygen carrier, without using CO.

The present invention has been made to solve these problems. As a result of intensive studies by the present inventors, it has been found that a metal complex of a deoxy form free of a CO bond, which has a porphyrin structure, is extremely easily oxidized, and a considerable amount of oxidation reaction occurs due to a substitution fluid used for ultrafiltration, dialyzing fluid used for dialysis and the like in a purification step of a complex of albumin and a metal complex having a porphyrin structure. Furthermore, they have found that the above-mentioned problems can be solved by producing a complex of albumin and a deoxy form metal complex having a porphyrin structure and preferably adding a reducing agent to a substitution fluid or a dialyzing fluid used for a purification step under a gas atmosphere substantially free of carbon monoxide (CO) and oxygen (hereinafter $O_2$), and completed the present invention.

Accordingly, the present invention provides (1) a method of producing a complex of albumin and a deoxy form metal complex having a porphyrin structure, which comprises mixing albumin and a metal complex having a porphyrin structure under a gas atmosphere substantially free of carbon monoxide and oxygen, (2) the production method of (1), which comprises converting an oxy form metal complex having a porphyrin structure to a deoxy form metal complex having a porphyrin structure and mixing the resulting complex with albumin, (3) the production method of (2), wherein the oxy form metal complex having a porphyrin structure is converted to the deoxy form metal complex having a porphyrin structure in the presence of a reducing agent, (4) the production method of (2), wherein the oxy form metal complex having a porphyrin structure is converted to the deoxy form metal complex having a porphyrin structure by nitrogen replacement, (5) the production method of (1), wherein, in the step of mixing albumin and a metal complex having a porphyrin structure, a central metal of the metal complex having a porphyrin structure is of a reduction type, (6) the production method of (1), wherein an aqueous albumin solution after removal of dissolved oxygen is added into a sealed container filled with a gas substantially free of carbon monoxide and oxygen, and then mixing a solution of a metal complex having a porphyrin structure in an organic solvent and a reducing agent, (7) the production method of (1), wherein the metal complex having a porphyrin structure is a heme derivative, (8) the production method of (1), wherein the gas is an inert gas, (9) the production method of (8), wherein the inert gas is one or more kinds of gases selected from the group consisting of hydrogen, helium, argon, nitrogen and neon,

(10) the production method of (3), wherein the reducing agent is one or more kinds selected from the group consisting of dithionous acid, sodium dithionite, sodium hydrogen sulfite, sodium sulfite, dry sodium sulfite, sodium pyrosulfite, sodium metabisulfite, Rongalite, L-ascorbic acid, sodium L-ascorbate, erythorbic acid, sodium erythorbate, cysteine, thioglycerol, α-thioglycerine, sodium edetate, citric acid, isopropyl citrate, potassium dichloroisocyanurate, sodium thioglycolate, sodium thiomalate, sodium 1,3-butylene glycol pyrosulfite, butylhydroxyanisole, dibutylhydroxytoluene, propyl gallate, ascorbyl palmitate, vitamin E related agent, dl-α-tocopherol, tocopherol acetate, natural vitamin E, d-δ-tocopherol, mixed tocopherol concentrate, guaiac resin, nordihydroguaiaretic acid, L-ascorbyl stearate, soybean lecithin, palmitic ascorbic acid, benzotriazole, pentaerythrityl-tetrakis[3-(3,5-di-t-butyl-4-hydroxyphenyl)propionate]2-mercaptobenzimidazole, calcium disodium ethylenediamine tetraacetate and disodium ethylenediamine tetraacetate,

(11) the production method of (6), wherein the organic solvent is ethanol,

(12) a method of purifying the complex obtained by the method of (1), which comprises ultrafiltration using, as a substitution fluid, an aqueous solution containing a reducing agent and/or free of oxygen,

(13) a method of purifying the complex obtained by the method of (1), which comprises dialysis using, as a dialyzing fluid, an aqueous solution containing a reducing agent and/or free of oxygen,

(14) a complex of albumin and a deoxy form metal complex having a porphyrin structure, which is obtained by the production method of (1),

(15) an artificial oxygen infusion preparation comprising the complex of (14) as it is, or as a carbon monoxide bound form or an oxygen bound form, which is filled in a preservation container, and

(16) the artificial oxygen infusion preparation of (15), further comprising one or more kinds selected from the group consisting of electrolyte, saccharide, pH adjuster solution, isotonicity agent and polymer imparting a colloid osmotic pressure.

Since the complex of albumin and a deoxy form metal complex having a porphyrin structure of the present invention is produced by steps free of CO, it can be used as a highly safe artificial oxygen carrier.

In addition, since the production method of the present invention obliterates the need for a strict CO leakage preventing management system, heretofore required by the production step of conventional artificial oxygen carriers, whereby production facility can be simplified and miniaturized.

When CO is used in a production step as in conventional cases, a step for removing CO is necessary before finally using the product as an oxygen carrier. For this end, an extremely intense light and oxygen are blown in, which may make a metal complex having a porphyrin structure an oxidation type, which may bring about a situation where the function as a carrier cannot be fulfilled. According to the production method of the present invention, a step for removing CO is not necessary because CO is not used in a production step, thus preventing degradation of the quality, which makes it possible to administer the carrier as it is in the case of emergency.

The complex of albumin and a deoxy form metal complex having a porphyrin structure of the present invention can be applied as an oxygen carrier to a wide range in the fields of medicine and pharmacy, and, like blood for infusion, can be used as it is or as a mixture containing additive as necessary as a blood substitute for clinical treatments.

In addition, the complex of albumin and a deoxy form metal complex having a porphyrin structure of the present invention can be intravenously administered as it is if a treatment for CO binding for long-term preservation is not applied. The administered complex of albumin and a deoxy form metal complex having a porphyrin structure immediately binds with oxygen when passing through the lung to become an oxy form and releases oxygen in peripheral blood vessels.

DETAILED DESCRIPTION OF THE INVENTION

Figure 1:
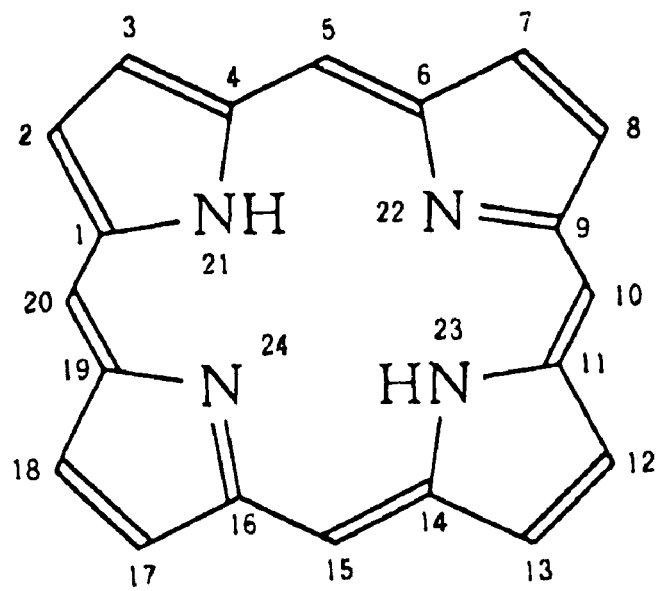
FIG. 1 explains a porphyrin ring.
Figure 2:
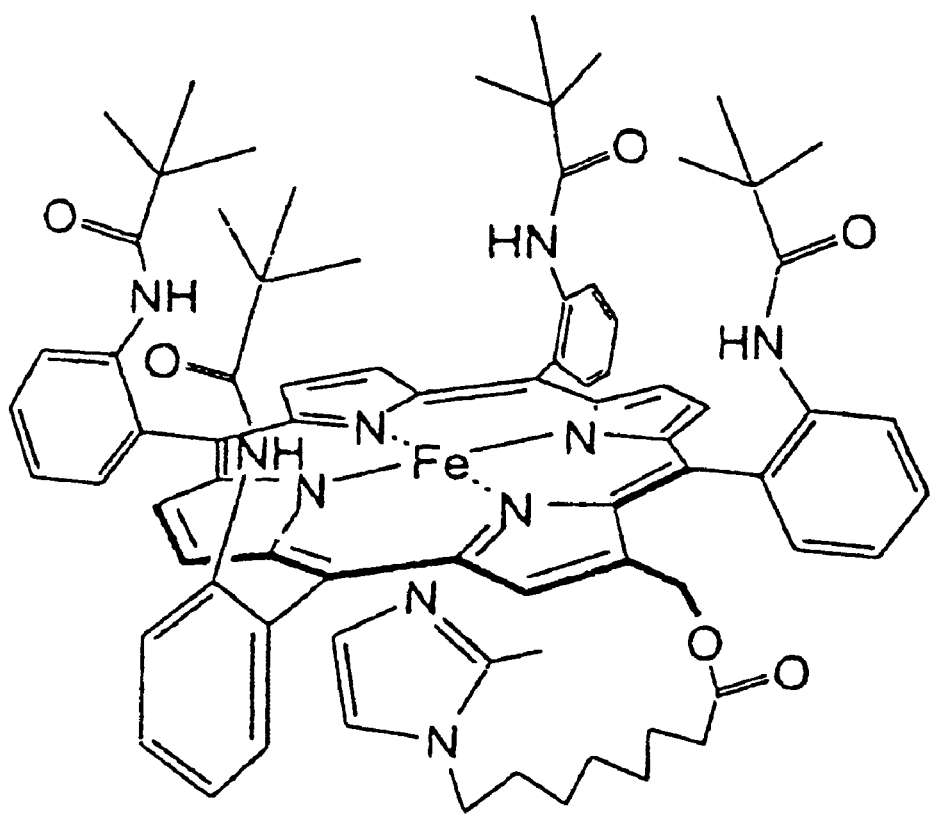
FIG. 2 explains one example of a porphyrin ring.

In the present invention, "a metal complex having a porphyrin structure" means a metal complex wherein a central metal is coordinated on a porphyrin ring, and it may contain a modified porphyrin ring or one having reversible binding capability with oxygen, all of which are encompassed thereby. The porphyrin ring means a macrocyclic compound wherein four pyrrole rings as shown in FIG. 1 are alternately bound to four methine groups at the α-position and its derivatives. A metal complex having a porphyrin structure is exemplified by one wherein the center of a porphyrin ring shown in FIG. 2 (2-[8-[N-(2-methlimidazolyl)]octanoyloxymethyl]-5,10,15,20-tetrakis (α,α,α,α-o-pivalamido)phenyl porphyrin) is coordinated with iron. The central metal of such metal complex is generally a transition element, preferably transition element of the 6-10 groups of the periodic table, and 4 period transition elements are more preferable. Of these, iron, cobalt, chromium and the like are preferable, more preferably iron (II) and cobalt (II).

In addition, a "deoxy form metal complex" means a metal complex wherein oxygen is not bound to the central metal, such as a metal complex wherein oxygen is not bound to the central metal, iron (II). An "oxy form metal complex" means a metal complex wherein oxygen is bound to the central metal, such as a metal complex wherein oxygen is bound to the central metal, iron (II).

In the present invention, a "metal complex having a porphyrin structure" is preferably a "heme derivative". A "heme derivative" means an iron complex having a porphyrin structure, which may be a derivative having a deformed porphyrin ring or one having reversible binding capability with oxygen, all of which are encompassed thereby. As a heme derivative, for example, tetraphenylporphyrin, protoporphyrin, octaalkyl porphyrin and their derivatives and the like can be mentioned. Of these, tetraphenylporphyrin is preferable.

In the present invention, a "complex of albumin and a deoxy form metal complex having a porphyrin structure" is obtained by binding albumin and a metal complex having a porphyrin structure, and has reversible adsorption and desorption capability of oxygen. For example, a complex of heme derivative and albumin (hereinafter albumin-heme) and the like can be mentioned.

A metal complex having a porphyrin structure wherein the central metal is of an oxidation type lacks reversible adsorption and desorption capability of oxygen. Therefore, it is necessary for a complex of albumin and a deoxy form metal complex having a porphyrin structure of the present invention to contain a reduction type central metal. However, it is difficult to convert a central metal of a metal complex having a porphyrin structure containing a central metal of an oxidation type (e.g., iron (III)) to a reduction type (e.g., iron (II)) after binding to albumin.

Therefore, when binding a metal complex having a porphyrin structure with albumin, the central metal of a metal complex having a porphyrin structure is preferably of a reduction type. For example, when binding an iron complex having a porphyrin structure with albumin, the central metal of the complex is preferably reduction type iron (II).

It is also possible to apply the idea of the present invention to a complex of albumin and a deoxy form metal complex having a porphyrin structure, as well as artificial oxygen carriers such as hemoglobin vesicle, lipid heme vesicle, lipid heme-triglyceride microsphere and the like, or a mixture or complex thereof and the like.

While the albumin to be used in the present invention is not particularly limited, for example, human serum albumin, serum albumin derived from animal, recombinant human serum albumin (rHSA), and multimers thereof and the like can be also mentioned. From the aspect of prevention of infection and the like, it is particularly preferably rHSA.

As examples of the albumin-heme of the present invention, one wherein a tetraphenylporphyrin iron derivative, 2-[8-[N-(2-methylimidazolyl)]octanoyloxymethyl]-5,10,15,20-tetrakis (α,α,α,α-o-pivalamido)phenylporphynatoiron complex, and the like are included in a hydrophobic pocket of albumin (E. Tsuchida, et al., Bioconjugate Chemistry, vol. 8, 534-538, 1997) and the like can be mentioned.

In the present invention, "a gas atmosphere substantially free of carbon monoxide and oxygen" means a gas atmosphere where a CO content is less than an amount influential on human body, and a $O_2$ content is lower than an amount that degrades a complex of albumin and a deoxy form metal complex having a porphyrin structure. This means that the presence of a small amount of carbon monoxide which is free of an influence on human body and the presence of oxygen in the range where the complex of albumin and a deoxy form metal complex having a porphyrin structure of the present invention can be obtained stably are tolerated. To be specific, the concentration of carbon monoxide in the above-mentioned gas atmosphere is preferably not more than 0.1 ppm, and the oxygen concentration in the above-mentioned gas atmosphere is preferably not more than 1% (ca. 10000 ppm), more preferably not more than 0.1% (ca. 1000 ppm), and still more preferably not more than 100 ppm.

A gas constituting the above-mentioned gas atmosphere is preferably an inert gas. An inert gas means a chemically inactive gas, such as rare gas such as helium, argon, neon and the like, and nitrogen and hydrogen. Use of nitrogen gas is industrially preferable.

As the reducing agent in the present invention, for example, dithionous acid, dithionite salt (sodium dithionite and the like), hydrogen sulfite salt (sodium hydrogen sulfite and the like), sulfite salt (sodium sulfite, dry sodium sulfite and the like), pyrosulfite salt (sodium pyrosulfite and the like), metabisulfite salt (sodium metabisulfite and the like), Rongalite ($CH_2OHSO_2Na$), ascorbic acid or a salt thereof (L-ascorbic acid, sodium L-ascorbate and the like), erythorbic acid or a salt thereof (sodium erythorbate and the like), cysteine (preferably cysteine hydrochloride), thioglycerol, α-thioglycerine, edetate salt (sodium edetate and the like), citric acid, isopropyl citrate, dichloroisocyanurate salt (potassium dichloroisocyanurate and the like), thioglycolate salt (sodium thioglycolate and the like), thiomalate salt (sodium thiomalate and the like), sodium 1,3-butylene glycol pyrosulfite, butylhydroxyanisole (BHA), dibutylhydroxytoluene (BHT), propyl gallate, ascorbyl palmitate, dl-α-tocopherol, tocopherol acetate, natural vitamin E, d-δ-tocopherol, mixed tocopherol concentrate, guaiac resin, nordihydroguaiaretic acid (NDGA), L-ascorbyl stearate, soybean lecithin, palmitic ascorbic acid, benzotriazole, pentaerythrityl-tetrakis[3-(3,5-di-t-butyl-4-hudroxyphenyl)propionate]2-mercaptobenzimidazole, calcium disodium ethylenediamine tetraacetate and disodium ethylenediamine tetraacetate can be mentioned. Of these, L-ascorbic acid and sodium L-ascorbate are preferable. Only one kind of reducing agent selected from such group may be used, or two or more kinds of reducing agents may be used simultaneously.

In the present invention, "nitrogen replacement" means an operation to remove oxygen by placing an object under a nitrogen atmosphere. For example, an oxy form metal complex having a porphyrin structure is placed under a nitrogen atmosphere to remove oxygen, thereby converting to a deoxy form metal complex having a porphyrin structure. As a method for nitrogen replacement, a method comprising bubbling a nitrogen gas into a solution of an object substance (hereinafter nitrogen bubble) and a method comprising spraying a nitrogen gas onto a surface of a solution of an object substance (nitrogen flow) can be mentioned.

The production method of the present invention preferably includes a step of adding an aqueous solution of albumin after removal of dissolved oxygen into a sealed container filled with a gas substantially free of carbon monoxide and oxygen, and then mixing a reducing agent with a solution of a metal complex having a porphyrin structure in an organic solvent.

The organic solvent to dissolve a metal complex having a porphyrin structure is not particularly limited as long as it can dissolve a metal complex having a porphyrin structure. Generally, a water-soluble organic solvent is used, with preference given to ethanol for use as a pharmaceutical product. While the amount of the metal complex having a porphyrin structure in an organic solvent solution can be adjusted according to the object of use, it is preferably about 1-10 mol per 1 mol of albumin. It is preferable to add the above-mentioned reducing agent to an organic solvent for a metal complex having a porphyrin structure.

A solution of a metal complex having a porphyrin structure in an organic solvent is subjected to nitrogen replacement in advance, such as nitrogen bubbling and the like, whereby, prior to mixing with an aqueous solution of albumin, an oxy form metal complex having a porphyrin structure is converted to a deoxy form metal complex having a porphyrin structure. The time of nitrogen bubbling is preferably about 1-30 min.

The concentration of an aqueous solution of albumin is preferably less than about 25% (w/w). When the concentration is low, the production efficiency becomes poor. Oxygen is preferably removed from an aqueous solution of albumin in advance, before mixing with a solution of a metal complex having a porphyrin structure in an organic solvent. For example, it is mixed with a solvent after removal of oxygen by nitrogen bubble and the like, and subjected to nitrogen flow as necessary to remove oxygen. The aforementioned solvent is not particularly limited as long as it can be used for the production of injection, and water for injection, physiological saline, buffer and the like can be mentioned. Direct bubbling of nitrogen in an aqueous solution of albumin unpreferably modifies albumin. The time of nitrogen bubble is preferably about 1-60 min.

For mixing of an organic solvent to solve a metal complex having a porphyrin structure with an aqueous solution of albumin, an aqueous solution of albumin is first added into a sealed container filled with a gas substantially free of carbon monoxide and oxygen, and then an organic solvent to dissolve a metal complex having a porphyrin structure is added by a small amount and the mixture is preferably mixed by stirring. The mixing is performed under temperature conditions of generally about 0-60° C., preferably about 10-50° C., so that freezing of aqueous solution and denaturing of albumin do not occur. The mixing time is a time necessary for uniformly mixing albumin and a metal complex having a porphyrin structure and obtaining a desired amount of a complex of albumin and a metal complex having a porphyrin structure.

In the present invention, "purified method of a complex of albumin and a deoxy form metal complex having a porphyrin structure" is a method of separating a solvent or an impurity in a solution containing a complex of albumin and a deoxy form metal complex having a porphyrin structure using various known blood purification methods and the like. For example, various known purification methods such as blood dialysis, blood dialysis filtration, blood filtration and the like can be applied. It is preferable to perform filtration using an ultrafiltration membrane by a blood filtration method and supplement a substitution fluid as necessary to a solution containing a complex of albumin and a deoxy form metal complex having a porphyrin structure. In addition, dialysis using a semipermeable membrane and a dialyzing fluid may be performed by a blood dialysis method. The substitution fluid or dialyzing fluid to be used here preferably an aqueous solution containing a reducing agent and/or free of oxygen. As the reducing agent, those similar to the ones to be added to the above-mentioned solvent for a metal complex having a porphyrin structure can be used, and as a method to remove oxygen, various known methods such as nitrogen bubble and the like can be used. By the use of such substitution fluid, oxygenation of a complex of albumin and a deoxy form metal complex having a porphyrin structure can be prevented.

The artificial oxygen infusion preparation obtained by the method of the present invention is a liquid containing a complex of albumin and a deoxy form metal complex having a porphyrin structure having oxygen transport capability.

The artificial oxygen infusion preparation of the present invention may contain, where necessary, a compound capable of providing a colloid osmotic pressure. As a compound capable of providing a colloid osmotic pressure, various polymers used for pharmaceutical agents can be used as long as they have a colloid osmotic pressure. Examples thereof include dextran (e.g., low molecular weight dextran), dextran derivative (e.g., carboxymethyl dextran, carboxy dextran, cationic dextran, dextran sulfate), hydroxyethylstarch, hydroxypropylstarch, gelatin (e.g., modified gelatin), albumin (e.g., human raw plasma, human serum albumin, human heated plasma protein, recombinant human serum albumin), PEG, polyvinylpyrrolidone, carboxymethyl cellulose, acacia rubber, glucose, dextrose (e.g., D-glucose monohydrate), oligosaccharides (e.g., oligosaccharide), polysaccharides degradation product, amino acid, protein degradation product and the like. Of these, low molecular weight dextran, hydroxyethylstarch, modified gelatin and recombinant albumin are particularly preferable.

The above-mentioned complex of albumin and a deoxy form metal complex having a porphyrin structure reversibly binds oxygen when a metal complex having a porphyrin structure is of a reduction type, but when it is of an oxidation type, the metal complex does not have oxygen binding capability. For example, when the central element iron of heme is a divalent iron ($Fe^{2+}$), the complex reversibly binds oxygen, but when it is of an oxidation type trivalent iron ($Fe^{3+}$), the complex does not have oxygen binding capability. Even a divalent iron complex bound with oxygen releases superoxide anion ($O_2^-$) and gradually autoxidized to become a trivalent iron (metho form) without oxygen binding capability. Moreover, an adverse influence on living organism of easy release of heme and iron ion from a metho form is worried.

Therefore, when an artificial oxygen infusion preparation containing such complex of albumin and a deoxy form metal complex having a porphyrin structure is to be preserved, the oxidation reaction needs to be suppressed.

As a method for suppressing oxidation reaction, the reaction rate may be lowered simply by chilled preservation. By simple chilled preservation, however, trivalent iron gradually increases. To prevent this, a method comprising addition of a methemoglobin reduction enzyme system inherently present in the red blood cell, an enzyme that eliminates active oxygen catalase and superoxide dismutase, and the like is known. The preservation temperature may be −20° C. to 60° C., preferably 4 to 25° C., and the complex is preserved in a cool dark place.

For preservation free of oxygen, for example, the complex is directly sealed in a glass bottle, aluminum/polyethylene layer bag (aluminized polyethylene bag), placed in a container made of a material having extremely low oxygen permeability such as polyvinylidene chlorides, ethylene-vinyl alcohol copolymers and the like, or sealed in a plastic bag, which is then preferably placed in a container that does not permeate oxygen.

Furthermore, by preservation while blocking oxygen after removing oxygen in a container containing an artificial oxygen infusion, oxidation of a metal complex having a porphyrin structure and oxidation of other components such as lipid and the like can be suppressed. After an oxygen removal step, a suitable amount of reagent (antioxidant) that reacts with oxygen may be dispersed in a container housing an artificial oxygen infusion, for the purpose of further removing a trace amount of oxygen remaining in the solution. When a complex of albumin and a deoxy form metal complex having a porphyrin structure is dispersed in a solution, an antioxidant may be added to the solvent.

As the antioxidant, various antioxidants generally used for pharmaceutical agents can be used. Examples thereof include dithionous acid, sodium hydrogen sulfite, sodium sulfite, sodium pyrosulfite (e.g., sodium metabisulfite), Rongalite ($CH_2OHSO_2Na$), ascorbic acid, sodium ascorbate, erythorbic acid, sodium erythorbate, cysteine, acetylcysteine, cysteine hydrochloride, homocysteine, glutathione, thioglycerol, α-thioglycerine, sodium edetate, citric acid, isopropyl citrate, potassium dichloroisocyanurate, sodium thioglycolate, sodium thiomalate, sodium 1,3-butylene glycol pyrosulfite, calcium disodium ethylenediamine tetraacetate, disodium ethylenediamine tetraacetate, amino acid sulfite (e.g., L-lysin sulfite), butylhydroxyanisole (BHA), dibutylhydroxytoluene (BHT), propyl gallate, ascorbyl palmitate, vitamin E and derivatives thereof (e.g., dl-α-tocopherol, tocopherol acetate, natural vitamin E, d-δ-tocopherol, mixed tocopherol concentrate, trolox), guaiac resin, nordihydroguaiaretic acid (NDGA), L-ascorbyl stearate, soybean lecithin, palmitic ascorbic acid, benzotriazole, pentaerythrityl-tetrakis[3-(3,5-di-t-butyl-4-hydroxphenyl)propionate]2-mercaptobenzimidazole and the like. Of these, dithionous acid, sodium hydrogen sulfite, sodium sulfite, ascorbic acid, cysteine, acetylcysteine, dl-α-tocopherol, tocopherol acetate, glutathione and trolox are preferable.

In addition, the complex of albumin and a deoxy form metal complex having a porphyrin structure of the present invention may be preserved after CO binding. For example, when a metal complex having a porphyrin structure is a heme (iron complex), CO showing 200 times higher affinity for heme than does oxygen is bound and subjected to long-term preservation.

In this case, the amount of use of CO is preferably the minimum necessary from the aspects of safety and the like. For this end, for example, when a complex of albumin and a deoxy form metal complex having a porphyrin structure is an albumin-heme, it is preferable to fill, after inclusion reaction, the complex in a container and substitute the inside of the container with CO rather than operating in a CO atmosphere for a long time from preparation of a heme ethanol solution to inclusion in albumin as in a conventional manner. This reduces the amount of CO to be used to an amount far smaller than conventional amounts.

To be specific, for example, a method comprising adding an aqueous L-ascorbic acid solution to an ethanol solution of heme derivative, which is added to an aqueous solution of albumin after removal of dissolved oxygen in a sealed container while performing nitrogen replacement, stirring the mixture to allow generation of albumin-heme in a deoxy form, which is then placed under a CO atmosphere to allow binding of CO to the albumin-heme and preserved, can be mentioned.

EXAMPLES

The present invention is explained in detail by referring to examples, which are not to be construed as limitative.

Example 1

A 2-[8-[N-(2-methylimidazolyl)]octanoyloxymethyl]-5,10,15,20-tetrakis (α,α,α,α-o-pivalamido)phenylporphynatoiron complex was obtained by the method of Tsuchida, et al., Bioconjugate Chemistry, vol. 8, pp. 534-538, 1997.

An aqueous solution (4 µL) of L-ascorbic acid (1.2 mM) was added to an ethanol solution (2 mL) of this complex (3.0 mM) and reacted for 10 min in a sealed container with nitrogen replacement to give solution A.

Separately, solution B was prepared by adding recombinant human serum albumin (1.5 mM, 0.5 mL) to aqueous phosphoric acid solution (pH 8.1, 1.0 mM, 7.5 mL) after removal of dissolved oxygen by nitrogen bubble.

Then, solution A was added to solution B and the mixture was stirred at room temperature for about 5 min.

The mixture was applied to an ultrafiltration tool (Ultrafilter manufactured by Advantec: ultrafiltration molecular weight 50000) concentrated to 5 mL. Using phosphate buffer (pH 7.4, 1.0 mM, 50 mL) containing an aqueous solution (200 µL) of L-ascorbic acid (1.2 mM), ethanol was removed by constant volume ultrafiltration. This was concentrated to 2.0 mL and the obtained mixture was filled in a glass vial and sealed. The inside of the container was replaced with nitrogen.

In this way, a porphyrin metal complex-albumin complex (albumin concentration 5.38%, porphyrin concentration 3.24 mM) was obtained.

Experimental Example 1

Oxygen was flown into the dispersion obtained in Example 1 to give an oxy form. The visible absorption spectrum was $\lambda_{max}$ of 420 nm. This dispersion was diluted and a small amount of dithionous acid was added under a nitrogen atmosphere to give a deoxy form, whose visible absorption spectrum was $\lambda_{max}$ of 441 nm.

By repeating alternate aeration with oxygen and nitrogen, adsorption and desorption of oxygen was confirmed. As a result of observation based on electrophoresis, albumin was not denatured.

Example 2

In the same manner as in Example 1, 2-[8-[N-(2-methylimidazolyl)]octanoyloxymethyl]-5,10,15,20-tetrakis tetrakis ($\alpha,\alpha,\alpha,\alpha$-o-pivalamido)phenylporphynatoiron complex was obtained.

An aqueous solution (10 μL) of L-ascorbic acid (1.2 mM) was added to an ethanol solution (5 mL) of this complex (1.2 mM) and reacted for 10 min in a sealed container with nitrogen replacement to give solution A.

Separately, solution B was prepared by adding recombinant human serum albumin (1.5 mM, 0.5 mL) to aqueous phosphoric acid solution (pH 8.1, 1.0 mM, 24.5 mL) after removal of dissolved oxygen by nitrogen bubble.

Then, solution A was added to solution B and the mixture was stirred at room temperature for about 5 min.

The mixture was applied to an ultrafiltration tool (Ultrafilter manufactured by Advantec: ultrafiltration molecular weight 50000) concentrated to 5 mL. Using phosphate buffer (pH 7.4, 1.0 mM, 50 mL) containing an aqueous solution (200 μL) of L-ascorbic acid (1.2 mM), ethanol was removed by constant volume ultrafiltration. This was concentrated to 2.0 mL and the obtained mixture was filled in a glass vial and sealed. The inside of the container was replaced with nitrogen.

In this way, an object porphyrin metal complex-albumin complex (albumin concentration 4.344%, porphyrin concentration 3.55 mM) was obtained.

Experimental Example 2

Oxygen was flown into the dispersion obtained in Example 2 to give an oxy form. The visible absorption spectrum was $\lambda_{max}$ of 421.5 nm. This dispersion was diluted and a small amount of dithionous acid was added under a nitrogen atmosphere to give a deoxy form, whose visible absorption spectrum was $\lambda_{max}$ of 441.5 nm.

By repeating alternate aeration with oxygen and nitrogen, adsorption and desorption of oxygen was performed. As a result of observation based on electrophoresis, albumin was not denatured.

Example 3

In the same manner as in Example 1, 2-[8-[N-(2-methylimidazolyl)]octanoyloxymethyl]-5,10,15,20-tetrakis ($\alpha,\alpha,\alpha,\alpha$-o-pivalamido)phenylporphynatoiron complex was obtained.

An aqueous solution (20 μL) of L-ascorbic acid (1.2 mM) was added to an ethanol solution (1 mL) of this complex (1.5 mM) and reacted for 10 min in a sealed container with nitrogen bubbling to give solution A.

Separately, solution B was prepared by adding recombinant human serum albumin (0.375 mM, 0.5 mL) to aqueous phosphoric acid solution (pH 8.1, 1.0 mM, 4.5 mL) after removal of dissolved oxygen by nitrogen bubble.

Then, solution A was added to solution B and the mixture was stirred at room temperature for about 5 min.

The mixture was applied to an ultrafiltration tool (Ultrafilter manufactured by Advantec: ultrafiltration molecular weight 50000) concentrated to 5 mL. Using phosphate buffer (pH 7.4, 1.0 mM, 50 mL), ethanol was removed by constant volume ultrafiltration. This was concentrated to 0.5 mL and the obtained mixture was filled in a glass vial and sealed. The inside of the container was replaced with nitrogen.

In this way, an object porphyrin metal complex-albumin complex (albumin concentration 5.252%, porphyrin concentration 1.74 mM) was obtained.

Experimental Example 3

Oxygen was flown into the dispersion obtained in Example 3 to give an oxy form. The visible absorption spectrum was $\lambda_{max}$ of 421.5 nm. This dispersion was diluted 1/50, transferred to a cell for spectroscopy made of quartz and a small amount of dithionous acid was added under a nitrogen atmosphere to give a deoxy form, whose visible absorption spectrum was $\lambda_{max}$ of 440.5 nm.

By repeating alternate aeration with oxygen and nitrogen, adsorption and desorption of oxygen was performed. As a result of observation based on electrophoresis, albumin was not denatured.

Example 4

In the same manner as in Example 1, 2-[8-[N-(2-methylimidazolyl)]octanoyloxymethyl]-5,10,15,20-tetrakis ($\alpha,\alpha,\alpha,\alpha$-o-pivalamido)phenylporphynatoiron complex was obtained.

An aqueous solution (4 μL) of L-ascorbic acid (1.2 mM) was added to an ethanol solution (5 mL) of this complex (1.2 mM) and reacted for 10 min in a sealed container with nitrogen bubbling to give solution A.

Separately, solution B was prepared by adding recombinant human serum albumin (1.5 mM, 0.5 mL) to aqueous phosphoric acid solution (pH 8.1, 1.0 mM, 24.5 mL) after removal of dissolved oxygen by nitrogen bubble.

Then, solution A was added to solution B and the mixture was stirred at room temperature for about 5 min.

The mixture was applied to an ultrafiltration tool (Ultrafilter manufactured by Advantec: ultrafiltration molecular weight 50000) concentrated to 5 mL. Using phosphate buffer (pH 7.4, 1.0 mM, 50 mL), ethanol was removed by constant volume ultrafiltration. This was concentrated to 2.0 mL and the obtained mixture was filled in a glass vial and sealed. The inside of the container was replaced with CO.

In this way, an object porphyrin metal complex-albumin complex (albumin concentration 5.041%, porphyrin concentration 2.71 mM) was obtained.

Experimental Example 4

By light irradiation (500 W) in an ice bath while flowing oxygen into the dispersion obtained in Example 4, an oxy form was obtained. The visible absorption spectrum was $\lambda_{max}$ of 421.5 nm. This dispersion was diluted, transferred to a cell for spectroscopy made of quartz and a small amount of dithionous acid was added under a nitrogen atmosphere to give a deoxy form, whose visible absorption spectrum was $\lambda_{max}$ of 441.5 nm.

By repeating alternate aeration with oxygen and nitrogen, adsorption and desorption of oxygen was performed. As a result of observation based on electrophoresis, albumin was not denatured.

Example 5

In the same manner as in Example 1, 2-[8-[N-(2-methylimidazolyl)]octanoyloxymethyl]-5,10,15,20-tetrakis (α,α,α,α-o-pivalamido)phenylporphynatoiron complex was obtained.

An aqueous solution (20 μL) of L-ascorbic acid (1.2 mM) was added to an ethanol solution (1 mL) of this complex (1.5 mM) and reacted for 10 min in a sealed container with nitrogen bubbling to give solution A.

Separately, solution B was prepared by adding recombinant human serum albumin (0.375 mM, 0.5 mL) to aqueous phosphoric acid solution (pH 8.1, 1.0 mM, 4.5 mL) after removal of dissolved oxygen by nitrogen bubble.

Then, solution A was added to solution B and the mixture was stirred at room temperature for about 5 min.

The mixture was applied to an ultrafiltration tool (Ultrafilter manufactured by Advantec: ultrafiltration molecular weight 50000) concentrated to 5 mL. Using phosphate buffer (pH 7.4, 1.0 mM, 50 mL), ethanol was removed by constant volume ultrafiltration. This was concentrated to 0.5 mL and the obtained mixture was filled in a glass vial and sealed. The inside of the container was replaced with nitrogen.

In this way, an object porphyrin metal complex-albumin complex (albumin concentration 3.16%, porphyrin concentration 3.90 mM) was obtained.

Experimental Example 5

Oxygen was flown into the dispersion obtained in Example 3 to give an oxy form. The visible absorption spectrum was $\lambda_{max}$ of 421.5 nm. This dispersion was diluted and a small amount of dithionous acid was added under a nitrogen atmosphere to give a deoxy form, whose visible absorption spectrum was $\lambda_{max}$ of 442.0 nm.

By repeating alternate aeration with oxygen and nitrogen, adsorption and desorption of oxygen was performed. As a result of observation based on electrophoresis, albumin was not denatured.

The artificial oxygen infusion preparation of the present invention can be used in any field requiring an oxygen carrier. For example, it is administered to living organisms for supply of oxygen to ischemic penumbra or tumor tissue, blood infusion during hemorrhage, or can be used as an organ preservation perfusate, a solution for extracorporeal circulation or a cell culture fluid.

This application is based on patent application No. 2003-305036 filed in Japan, the contents of which are hereby incorporated by reference.

What is claimed is:

1. A method of producing a complex of albumin and a deoxy form metal complex having a porphyrin structure and a reduction type iron (II) central metal,
   which comprises mixing albumin and a metal complex having a porphyrin structure and a reduction type iron (II) central metal under a gas atmosphere,
   wherein the concentration of carbon monoxide is not more than 0.1 ppm and the concentration of oxygen is not more than 1%.

2. The production method of claim 1, which comprises converting an oxy form metal complex having a porphyrin structure to a deoxy form metal complex having a porphyrin structure and mixing the resulting complex with albumin.

3. The production method of claim 2, wherein the oxy form metal complex having a porphyrin structure is converted to the deoxy form metal complex having a porphyrin structure in the presence of a reducing agent.

4. The production method of claim 2, wherein the oxy form metal complex having a porphyrin structure is converted to the deoxy form metal complex having a porphyrin structure by nitrogen replacement.

5. The production method of claim 1, wherein an aqueous albumin solution after removal of dissolved oxygen is added into a sealed container filled with a gas substantially free of carbon monoxide and oxygen, and then mixing a solution of a metal complex having a porphyrin structure in an organic solvent and a reducing agent.

6. The production method of claim 1, wherein the metal complex having a porphyrin structure is a heme derivative.

7. The production method of claim 1, wherein the gas atmosphere comprises one or more kinds of gases selected from the group consisting of hydrogen, helium, argon, nitrogen and neon.

8. The production method of claim 3, wherein the reducing agent is one or more kinds of agents selected from the group consisting of dithionous acid, sodium dithionite, sodium hydrogen sulfite, sodium sulfite, dry sodium sulfite, sodium pyrosulfite, sodium metabisulfite, Rongalite, L-ascorbic acid, sodium L-ascorbate, erythorbic acid, sodium erythorbate, cysteine, thioglycerol, α-thioglycerine, sodium edetate, citric acid, isopropyl citrate, potassium dichloroisocyanurate, sodium thioglycolate, sodium thiomalate, sodium 1,3-butylene glycol pyrosulfite, butylhydroxyanisole, dibutylhydroxytoluene, propyl gallate, ascorbyl palmitate, vitamin E related agent, dl-α-tocopherol, tocopherol acetate, natural vitamin E, d-δ-tocopherol, mixed tocopherol concentrate, guaiac resin, nordihydroguaiaretic acid, L-ascorbyl stearate, soybean lecithin, palmitic ascorbic acid, benzotriazole, pentaerythrityl-tetrakis[3-(3,5-di-t-butyl-4-hydroxyphenyl)propionate]2-mercaptobenzimidazole, calcium disodium ethylenediamine tetraacetate and disodium ethylenediamine tetraacetate.

9. The production method of claim 5, wherein the organic solvent is ethanol.

10. The production method of claim 1 further comprising the subsequent step of purifying the complex by ultrafiltration using, as a substitution fluid, an aqueous solution that contains a reducing agent and/or is free of oxygen.

11. The production method of claim 1 further comprising the subsequent step of purifying the complex by dialysis using, as a dialyzing fluid, an aqueous solution that contains a reducing agent and/or is free of oxygen.

* * * * *